United States Patent [19]

Kelly et al.

[11] Patent Number: 4,810,486
[45] Date of Patent: Mar. 7, 1989

[54] BONE-SEEKING COMPLEXES OF TECHNETIUM-99M

[75] Inventors: James D. Kelly, Amersham; David V. Griffiths, Keele, both of England

[73] Assignee: Amersham International plc., Little Chalfont, England

[21] Appl. No.: 160,605

[22] PCT Filed: Jun. 29, 1987

[86] PCT No.: PCT/GB87/00456
§ 371 Date: Feb. 29, 1988
§ 102(e) Date: Feb. 29, 1988

[87] PCT Pub. No.: WO88/00061
PCT Pub. Date: Jan. 14, 1988

[30] Foreign Application Priority Data

Jun. 30, 1986 [GB] United Kingdom ............... 8615916

[51] Int. Cl.$^4$ .................. A61K 49/02; C07F 9/38
[52] U.S. Cl. .................. 429/1.1; 534/14; 260/502.4 P
[58] Field of Search ............. 424/1.1; 534/14; 260/502.4 P

[56] References Cited

U.S. PATENT DOCUMENTS 3,965,254  6/1976  Tofe et al. .................. 424/1.1
4,104,366  8/1978  Schmidt-Dwuyer et al. ...... 424/1.1
4,504,462  3/1985  Van Duzee et al. ........... 424/1.1

*Primary Examiner*—John S. Maples
*Attorney, Agent, or Firm*—Wenderoth, Lind & Ponack

[57] ABSTRACT

A composition for use in the preparation of a bone-scanning agent comprises a mixture of a bis-phosphonic acid of formula (I), wherein $R^1$ and $R^3$ may be the same or different group selected from H, —SO$_3$H and a lower aliphatic group which may optionally contain one or more hetero atoms and which contains at least one —SO$_3$H group; $R^2$ is a group selected from H, —OH, —NH$_2$, —NHMe, —NMe$_2$ and lower alkyl optionally substituted by one or more polar groups; $R^4$ is a group selected from H, —OH, —NH$_2$, —NHMe, —NMe$_2$, —SO$_3$H and a lower alkyl optionally substituted by one or more polar groups; and n is 0 or 1; with the proviso that when n is 0, $R^1$ is not H and that when n is 1, $R^1$ and $R^3$ cannot both be H; or a non-toxic salt thereof, together with a reducing agent for pertechnetate ions. Technetium-99m, as an aqueous solution of pertechnetate ions, is added to the composition to form a complex of Tc-99m, and the bisphosphonate. The complex is useful as a bone-scanning agent and is rapidly taken up in bone to give scans of high definition.

11 Claims, No Drawings

BONE-SEEKING COMPLEXES OF TECHNETIUM-99M

The present invention relates to bone-seeking complexes of technetium-99m, methods of preparing said complexes and compositions for use in the preparation of said complexes.

In April 1971, G. Subramanian and J. G. McAfee described (Radiology, 99, 192-6) a bone scanning agent prepared by reducing pertechnetate $TcO_4$- with stannous chloride in the presence of tripolyphosphate. The resulting labelled complex gave good skeletal uptake but suffered from several disadvantages, the most important of which were a 24-hour delay between injection and scanning (so that high levels of radioactivity were required in order to obtain adequate instrument response), and the instability of the tripolyphosphate with respect to hydrolysis.

An intensive search in the 1970's for better phosphate- and phosphonate-based bone scanning agents has resulted in a large number of publications and several commercial products. The most widely used compound is methylene diphosphonate (MDP), the complex of which with tin and Technetium-99m is the subject of U.S. Pat. No. 4032625. Recent introductions to the market have included hydroxymethylene diphosphonate (HDP), which is the subject of European Patent Application No. 7676; and 1,1-diphosphonopropane-2,3-dicarboxylic acid (DPD), which is described in German O.S. No. 2755874.

A successful bone scanning agent requires inter alia high and rapid uptake of the agent in bone with rapid clearance from the blood and soft tissues such as muscle of that part of the agent not taken up in the bone. In order to achieve scans of high definition, current bone agents normally require an interval of two hours or even more between injection of the agent into the patient and performance of the scan. (The word "scan" is here taken to include gamma-camera imaging techniques). Even small reductions of the interval between injection and scanning are highly desirable and could lead to worthwhile increases in convenience to the patient and the physician and in the efficiency in the running of nuclear medicine units.

The present invention arises from our discovery of some new bone-scanning agents based on the use of some bis-phosphonic acid compounds which additionally contain one or more sulphonic acid groups.

In a first aspect, the present invention provides a composition for the preparation of a bone-scanning agent which comprises a mixture of a bis-phosphonic acid having the general formula

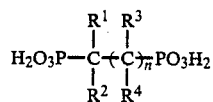
(I)

wherein:
$R^1$ and $R^3$ may be the same or different group selected from H, —$SO_3H$ and a lower aliphatic group which may optionally contain one or more hereto atoms and which contains at least one —$SO_3H$ group;
$R^2$ is a group selected from H, —OH, —$NH_2$, —NHMe, —$NMe_2$ and lower alkyl optionally substituted by one or more polar groups;
$R^4$ is a group selected from H, —OH, —$NH_2$ —NHMe, —$NMe_2$, —$SO_3H$ and lower alkyl optionally substituted by one or more polar groups; and
n is 0 or 1; with the proviso that when n is 0, $R^1$ is not H and that when n is 1, $R^1$ and $R^3$ cannot both be H; or a non-toxic salt thereof together with a reducing agent for pertechnetate ions.

In a second aspect, the present invention provides a method of preparing a technetium-99m-labelled bone scanning agent comprising adding technetium-99m, as an aqueous solution of pertechnetate ions to a composition comprising a mixture of a bis-phosphonic acid compound of the formula I above, or a non-toxic salt thereof, and a reducing agent for pertechnetate ions.

In a third aspect, the present invention provides a bone-seeking composition which comprises an aqueous solution of a complex of technetium-99m and a bis-phosphonic acid compound having the formula I above or a non-toxic salt thereof.

The bis-phosphonic acid complexing agent of the formula I above is either a gem-bisphosphonate (in the case where n=0) or a vic-bisphosphonate (in the case where n=1). The gem-biphosphonates have the general formula II

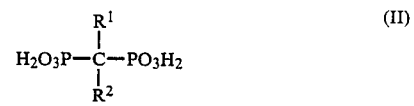

wherein $R^1$ is —$SO_3H$ or a lower aliphatic group, which may optionally contain one or more hetero atoms, and which contains at least one —$SO_3H$ group and $R^2$ is H, —OH, —$NH_2$, —NHMe, —$NMe_2$ or a lower alkyl group optionally substituted by one or more polar groups. Preferably, the group $R^1$ is a lower aliphatic group, having from 1 to 6 carbon atoms, optionally containing a hetero atom, such as N in the carbon chain, which contains one or two —$SO_3H$ groups and which may, in addition, contain one or more other polar substituents, e.g. —OH, —$NH_2$, —NHMe, —$NMe_2$ and —COOH, attached to carbon atoms of the group. Examples of suitable $R^1$ groups include the groups of the formula —$CH_2N(CH_2SO_3H)_2$ and $(CH_2)_m$ $SO_3H$, where m is 1 to 6, especially —$CH_2SO_3H$. The group $R^2$ in formula II above is H, —OH, —$NH_2$, —NHMe, —$NMe_2$ or a lower alkyl optionally substituted by one or more polar groups. The lower alkyl group for $R^2$ is typically a 1—6C alkyl group and preferably a methyl or ethyl group substituted by one or more polar groups. Examples of suitable substituent polar groups are —OH, —$NH_2$, —NHMe, —$NMe_2$ and —COOH groups.

As mentioned above, formula I relates to vic-bisphosphonates when n=1. Preferred vic-bisphosphonates suitable for use in the present invention are those having the following general formula III:

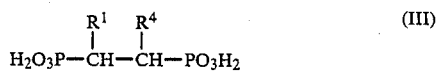

wherein
$R^1$ is —$SO_3H$ or —$CH_2SO_3H$ and
$R^4$ is H, —OH, —$NH_2$, —NHMe, —$NMe_2$, —$SO_3H$ or a lower alkyl optionally substituted by one or more polar groups. In the case when $R^4$ is an optionally substituted lower alkyl group it typically has from 1 to 6 carbon atoms and preferably is methyl or ethyl substituted by one or more polar substituents. Examples of suitable polar groups are —OH, —NH$_2$, —NHMe, —NMe$_2$ and —COOH groups.

Preferably, the bisphosphonates of formula I above used in the present invention contain fewer than 6 carbon atoms, in total, per molecule.

Representative compounds of the formula I above include the following:

(1) diphosphonomethane sulphonic acid;
(2) 2,2-diphosphonoethanesulphonic acid;
(3) 2,2-diphosphono-2-hydroxyethanesulphonic acid;
(4) 1,1-diphosphono-2-hydroxyethanesulphonic acid.
(5) N,N-disulphonomethyl-1-aminoethane-1,1-diphosphonic acid.

The preferred complexing agent of the invention is 2,2-diphosphonoethane sulphonic acid which shows high and rapid uptake in bone without any apparent concomitant disadvantages.

2,2-diphosphonoethane sulphonic acid (2-sulphoethane-1,1-diphosphonic acid), is believed to be a new compound and, accordingly, this forms a further aspect of the invention. This compound, as its sodium salt, may be prepared according to the following reaction scheme:

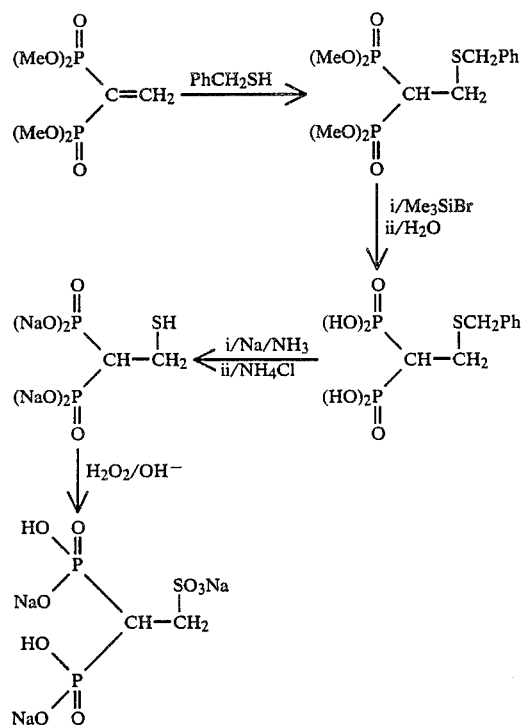

The composition of the present invention for the preparation of the bone-scanning agent may be prepared simply by mixing an aqueous solution of the bisphosphonic acid complexant, or a non-toxic salt thereof, with a solution of the reducing agent and the pH of the mixture may, if desired, be adjusted within the range of from 3 to 9, preferably 4 to 8. If desired, the mixture may be dispersed into sealed vials, freeze dried and, if not already sterile, finally sterilized.

Known reducing agents for pertechnetate include tin (2+), iron (2+) and chromium (2+) salts, as well as metallic tin. Tin, as the metal, or more particularly as a stannous salt, is the most widely used reducing agent for this purpose and is preferred in the present invention.

When the reducing agent is a stannous salt, the use of the biphosphonic acid or its non-toxic salt in a molar excess over the salt helps stabilise the composition. When stannous chloride is used as the reducing agent, it may be used in the preparation of the composition as an ethanolic solution in order to minimise problems due to hydrolysis. The composition may also include an inert bulking agent to aid the dispersing of small amounts of the composition into individual vials. In addition, other known additives may be included in the compositions, such as the stabilising agents nitrate, nitrite or para-aminobenzoic acid.

A preferred formulation of the composition of the invention will contain from 0.1 to 1.0 mg stannous chloride with from 1 to 50 mg of 2,2-diphosphonoethane sulphonic acid or its sodium salt thereof, in a vial for activation by from 1 to 15 ml of saline eluate from a technetium-99m generator.

In addition to the composition of the invention of an aqueous solution of pertechnetate ions, the technetium in the pertechnetate ions is reduced by the reducing agent from the 7+ state to a lower oxidation state in which it complexes with the bis-phosphonic acid compound of the formula I, or the non-toxic salt thereof. The exact nature of the complexes formed are not known and the reducing agent may also possibly be involved in the complex.

EXAMPLE I

Preparation of 2-sulphoethane-1,1-diphosphonic acid, sodium salt.

i. Tetramethyl 2-benzylthioethane-1,1-diphosphonate.

Tetramethyl ethene-1,1-diphosphonate (2.15 g) was added to a solution of benzyl mercaptan (1.09 g) in chloroform (10 cm$^3$) and the mixture then heated at 70° C. After 24 h at this temperature the reaction was complete. The volatile components were removed under reduced pressure to give the desired product (2.9 g; 89%). This material was sufficiently pure to be used without further purification.

$\delta(^{31}P)$ (CDCl$_3$) 23.6 (m).

$\delta(^{1}H)$ (CDCl$_3$) 2.4–3.2 (3H, m), 3.67 (2H), 3.70 (12H, d, 12 Hz), 7.18 (5H).

$\delta(^{13}C)$ (CDCl$_3$) 25.4, 35.3, 35.8 (t, 130 Hz), 51.6 (4C, m), 125.4, 126.8 (2C), 127.3 (2C), 136.4.

ii. 2-Benzylthioethane-1,1-diphosphonic acid.

Tetramethyl 2-benzylthioethane-1,1-diphosphonate (2.45 g) in chloroform (5 cm$^3$) was treated with an excess of trimethylsilyl bromide (5.1 g) at room temperature. The formation of the trimethylsilyl esters was monitored by $^{31}P$ n.m.r. and was complete after 15 min.

$\delta(^{31}P)$ (CDCl$_3$) 3.1 (d of t, 25 and 16 Hz).

$\delta(^{1}H)$ (CDCl$_3$) 0.35 (36H), 1.8–3.2 (3H, m), 3.69 (2H), 7.15 (5H).

The chloroform and excess trimethylsilyl bromide were removed under reduced pressure and water (20 cm$^3$) was then added. The mixture was stirred to give a clear solution consisting of two layers. The excess water and trimethylsilyl alcohol were removed under reduced pressure to yield the diphosphonic acid (1.75 g; 84%).

$\delta(^{31}P)$ (D$_2$O) 19.4 (d of t, 23 and 15 Hz).

iii. 2-Mercaptoethane-1,1-diphosphonic acid, sodium salt

2-Benzylthioethane-1,1-diphosphonic acid, sodium salt (1 g) was dissolved in liquid ammonia (25 cm³) in a flask equipped with a magnetic stirrer, acetone/solid CO₂ condenser and soda-lime guard tube, and cooled in an acetone/solid CO₂ bath. Sodium was then added in small portions until the deep blue colouration persisted for longer than 1 h. At this time excess reductant was quenched by the addition of solid ammonium chloride. The cooling bath and condenser were removed and the ammonia was allowed to evaporate. The residue was taken up into water and the product precipitated by the addition of ethanol.

$\delta(^{31}P)$ (D₂O) 17.7 (d of t, 22 and 16 Hz).
$\delta(^{13}C)$ (D₂O) 22.8, 48.5 (t, 115 Hz).

iv. 2-Sulphoethane-1,1-diphosphonic acid.

The crude 2-mercaptoethane-1,1-diphosphonic acid (500 mg) from the previous reaction was dissolved in water (3 cm³) and sodium hydroxide added until the pH of the solution was approximately 10. Hydrogen peroxide (2 cm³; 100 vol) was added to this solution. The oxidation was monitored by ³¹P n.m.r. and was complete after 15 min. Acetone was added to the solution which caused a viscous oil to separate out. The supernatant liquid was decanted off, the residue was taken up into water, and the desired product precipitated by the addition of ethanol. This process was repeated until the product was pure, as indicated by ³¹ n.m.r. spectroscopy. The compound was obtained as a white solid with an elemental analysis consistent with that of the trisodium salt.

$\delta(^{31}P)$ (D₂O) 19.1 (d of t, 22 and 15 Hz).
$\delta(^{13}C)$ (D₂O) 37.2 (t, 117 Hz), 51.2.

EXAMPLE II

The biodistributions in rats of a composition containing 2-sulphoethane-1,1-diphosphonic acid were determined by the following procedure.

Formulation A 1.5 mg of 2-sulphoethane-1,1-diphosphonic acid 70 μl of 3 mg/ml SnCl₂.2H₂O in ethanol made up to a total volume of 3 ml with 10 mCi NaTcO₄⁻ in 0.9% NaCl, the pH being 4.5.

The preparation was injected (injection volume was 100 μl) into each rat. After 15 minutes from injection had elapsed, the rats were sacrificed and dissected. The activity uptake in the bone, blood, muscle, liver and spleen of each rat was measured. Results obtained, together with results obtained for typical formulations containing methylene diphosphonate (MDP) are presented in the following Table. In the Table, the abbreviations B/M, B/Bl and B/L+S represent the activity ratios for bone/muscle, bone/blood and bone/liver+spleen.

TABLE

| FORMULATION | No. of animals | Biodistribution Study Mean (Sd *) | | | |
|---|---|---|---|---|---|
| | | Bone | B/M | B/Bl | B/L + S |
| Medronate II | 49 | 36.5 (3.2) | 41.1 (9.8) | 10.4 (2.2) | 25.9 (14.5) |
| A | 1 | 38.1 | 53.7 | 13.1 | 45.4 |
| A | 1 | 37.9 | 32.4 | 10.1 | 34.9 |
| A | 1 | 34.4 | 42.9 | 10.5 | 43.7 |
| A | Mean of 3, ± S.D.* | 36.8 ± 2.1 | 43.0 ± 10.6 | 11.2 ± 1.7 | 41.3 ± 5.7 |

*S.D. = standard deviation

The Medronate II used was a freeze dried formulation requiring only the addition of sodium pertechnetate 0.9% saline from a generator. The formulation was, per vial:

5 mg: MDP (as sodium salt)
0.340 mg: SnF₂
2 mg: sodium p-aminobenzoate.

We claim:

1. A composition for use in the preparation of a bone-scanning agent which comprises a mixture of bis-phosphonic acid having the general formula (I):

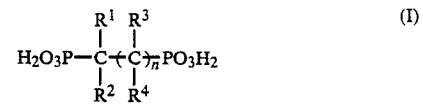

wherein

R¹ and R³ may be the same or different group selected from H, —SO₃H and a lower aliphatic group which may optionally contain one or more hetero atoms and which contains at least one —SO₃H group;

R² is a group selected from H, —OH, —NH₂, —NHMe, —NMe₂ and lower alkyl optionally substituted by one or more polar groups;

R⁴ is a group selected from H, —OH, —NH₂, —NHMe, —NMe₂, —SO₃H and a lower alkyl optionally substituted by one or more polar groups; and n is 0 or 1; with the proviso that when n is 0, R¹ is not H and that when n is 1, R¹ and R³ cannot both be H; or a non-toxic salt thereof, together with a reducing agent for pertechnetate ions.

2. A composition as claimed in claim 1 which comprises a mixture of a bis-phosphonic acid having the general formula II:

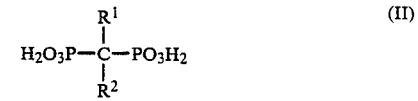

wherein

R¹ is —SO₃H or a lower aliphatic group containing from 1 to 6 carbon atoms and which contains one or two —SO₃H groups, and R² is as defined in claim 1; or a non-toxic salt thereof; together with a reducing agent for pertechnetate ions.

3. A composition as claimed in claim 2 wherein the group R¹ in the bis-phosphonic acid II is —CH₂N(CH₂SO₃H)₂ or (CH₂)ₘSO₃H, where m is an integer from 1 to 6.

4. A composition as claimed in claim 3 wherein the bis-phosphonic acid is 2,2-diphosphonoethanesulphonic acid.

5. A composition as claimed in claim 1 which comprises a mixture of a bis-phosphonic acid having the general formula III:

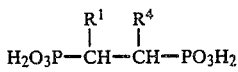   (III)

wherein
$R^1$ is $-SO_3H$ or $-CH_2SO_3H$ and
$R^4$ is H, $-OH$, $-NH_2$, $-NHMe$, $-NMe_2$, $-SO_3H$, or a lower alkyl optionally substituted by one or more polar groups; or a non-toxic salt thereof, together with a reducing agent for pertechnetate ions.

6. A composition as claimed in claim 1, wherein the reducing agent for pertechnetate ions is a non-toxic salt of tin (2+), iron (2+) or chromium (2+) or is metallic tin.

7. A composition as claimed in claim 6, wherein the reducing agent is selected from stannous chloride and stannous fluoride.

8. A method of preparing a technetium-99m labelled bone scanning agent comprising adding technetium-99m, as an aqueous solution of pertechnetate ions, to a composition as claimed in any one of claims 1 to 7.

9. A method as claimed in claim 8, wherein the pertechnetate ions are added as a solution in isotonic saline.

10. A bone-seeking composition comprising an aqueous solution of a complex of technetium-99m and a bis-phosphonic acid having the general formula I:

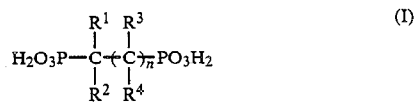   (I)

wherein
$R^1$ and $R^3$ may be the same or different group selected from H, $-SO_3H$ and a lower aliphatic group which may optionally contain one or more hetero atoms and which contains at least one $-SO_3H$ group;
$R^2$ is a group selected from H, $-OH$, $-NH_2$, $-NHMe$, $-NMe_2$ and lower alkyl optionally substituted by one or more polar groups;
$R^4$ is a group selected from H, $-OH$, $-NH_2$, $-NHMe$, $-NMe_2$, $-SO_3H$ and a lower alkyl optionally substituted by one or more polar groups; and
n is 0 or 1; with the proviso that when n is 0, $R^1$ is not H and that when n is 1, $R^1$ and $R^3$ cannot both be H; or a non-toxic salt thereof.

11. A bone-seeking composition as claimed in claim 10 which comprises an aqueous solution of a complex of technetium-99m and 2,2-diphosphonoethanesulphonic acid.

* * * * *